United States Patent
Abelev et al.

(10) Patent No.: US 8,763,470 B2
(45) Date of Patent: Jul. 1, 2014

(54) HIGH-CAPACITY WIDE-RANGE VARIABLE ROTATIONAL RATE VANE TESTING DEVICE

(71) Applicants: Andrei Abelev, Mclean, VA (US); David C Young, Long Beach, MS (US); Philip J. Valent, Slidell, LA (US)

(72) Inventors: Andrei Abelev, Mclean, VA (US); David C Young, Long Beach, MS (US); Philip J. Valent, Slidell, LA (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/945,644

(22) Filed: Jul. 18, 2013

(65) Prior Publication Data

US 2013/0298370 A1    Nov. 14, 2013

Related U.S. Application Data

(62) Division of application No. 13/106,166, filed on May 12, 2011, now Pat. No. 8,505,390.

(51) Int. Cl.
*G01N 3/24* (2006.01)
(52) U.S. Cl.
USPC .......................................................... 73/841
(58) Field of Classification Search
USPC .......................................................... 73/841
See application file for complete search history.

(56) References Cited

U.S. PATENT DOCUMENTS

| 3,364,734 A | 1/1968 | Wilson |
| 3,448,608 A | 6/1969 | Bishop et al. |
| 3,505,860 A | 4/1970 | Bishop et al. |
| 3,552,195 A | 1/1971 | Koprowski |
| 4,535,621 A | 8/1985 | Gervais et al. |
| 5,321,974 A | 6/1994 | Hemmings et al. |
| 5,438,863 A * | 8/1995 | Johnson .................... 73/54.02 |
| 5,565,620 A | 10/1996 | Bohlin |
| 6,539,809 B1 | 4/2003 | Weiss et al. |
| 6,571,609 B1 | 6/2003 | Bi |
| 7,275,419 B2 | 10/2007 | Raffer |
| 7,681,437 B2 | 3/2010 | Brinz et al. |
| 7,681,459 B1 | 3/2010 | Yang et al. |
| 8,505,390 B2 | 8/2013 | Young et al. |
| 2010/0116034 A1 | 5/2010 | Abbott et al. |
| 2012/0285256 A1 | 11/2012 | Young et al. |

OTHER PUBLICATIONS

H-60, Inspection vane tester user manual, Geonor A/S, Geonor, Inc., Milford, PA, pp. 1-7, Sep. 22, 2004 (from document properties).

Abelev, A., et al, U.S. Appl. No. 13/947,188, High-Capacity Wide-Range Variable Rotational Rate Vane Testing Device, Divisional of U.S. Appl. No. 13/106,166, filed Jul. 22, 2013.

(Continued)

*Primary Examiner* — Lisa Caputo
*Assistant Examiner* — Octavia Davis-Hollington
(74) *Attorney, Agent, or Firm* — US Naval Research Laboratory; Kathleen Chapman

(57) ABSTRACT

System and method for manufacturing an apparatus for measuring shear strength and viscosity of sediments that extends both the maximum rotational rate attainable and the maximum torque sustainable, and includes a high data acquisition rate and data storage. The apparatus can accurately measure, for example, but not limited to, peak, evolution, and residual values of the undrained shear strength, yield, and viscous and plastic flow (including hardening and softening) characteristics of cohesive sediments at various pre-set and variable values of the rotational velocity of the vane sensor.

20 Claims, 6 Drawing Sheets

(56) References Cited

OTHER PUBLICATIONS

Abelev, A., et al, U.S. Appl. No. 13/947,231, High-Capacity Wide-Range Variable Rotational Rate Vane Testing Device, Divisional of U.S. Appl. No. 13/106,166, filed Jul. 22, 2013.

Notice of Allowance, U.S. Appl. No. 13/106,166, NOA mailed on Apr. 15, 2013, filed on May 12, 2011.

Wykeham Farrance, Laboratory Vane Apparatus with a vane of 12.7 mm×12.7 mm configuration and set of four calibrated springs, Sep. 18, 2007, weblink.

Peterson, L.M., Johnson, G.W., and Babb, L.V., High Quality Sampling and in SITU testing for deepwater geotechnical site investigation, pp. 913-915, 1986.

Perlow, M., Jr., and Richards, A.F., Influence of Shear Velocity on Vane Shear Strength, Journal of Geotechnical Engineering Division, vol. 104, GT12, pp. 1517-1518, Dec. 1978.

Perlow, M., Jr., and Richards, A.F. Influence of Shear Velocity on Vane Shear Strength, Journal of the Geotechnical Engineering Division, pp. 19-32, Jan. 1977.

Perez-Foguet, A., Ledesma A. and Huerta, A., Analysis of the Vane Test Considering Size and Time Effects, International Journal for Numerical and Analytical Methods in Geomechanics, Int. J. Numer. Anal. Meth. Geomech, 23, pp. 383-412, 1999.

Poulos, H.G., Marine Geotechnics, School of Civil and Mining Engineering, University of Sydney, section 4.4, pp. 164-171, 1988.

Monney, N.T., Analysis of the Vane Shear Test at Varying Rates of Shear, Deep-Sea Sediments, Anton L. Inderbitzen, (ed), pp. 151-167, 1974.

Locat, J. and Demers, D., Viscosity, yield stress, remolded strength and liquidity index relationships for sensitive clays, Can. Geotech. J. 25, pp. 799-806, 1988.

Einav, I. and Randolph, M. Technical Note, Effect of strain rate on mobilised strength and thickness of curved shear bands, Geotechnique 56, No. 7, pp. 501-504, 2006.

Biscontin, G. and Pestana, J.M., Technical Note, Influence of Peripheral Velocity on Van Shear Strength of an Artificial Clay, Geotechnical Testing Journal, GTJODJ, vol. 24, No. 4, pp. 423-429, Dec. 2001.

Torstensson, B., Time-dependent effects in the field vane test, Geotechnical Aspects of Soft Clays: Proceedings of the International Symposium on Soft Clay, Brenner, R.P. and Brand, E.W. (eds), Asian Institute of Technology, Bankok, Thailand, pp. 387-397, Jul. 5-6, 1977.

ASTM, Designation: D 4648-05, Standard Test Method for Laboratory Miniature Vane Shear Test for Standard Fine-Grained Clayey Soil, ASTM International, 100 Bar Harbor, Dr., West Conshohocken, PA, 2005.

ASTM, Designation: D2573-08, Standard Test Method for Field Vane Shear Test for Saturated Cohesive Soil, ASTM International, 100 Bar Harbor, Dr., West Conshohocken, PA, 2008.

Brookfield Engineering Laboratories, Inc., R/S+ series Rheometers, www.bookfieldengineering.com, Mar. 13, 2009 (created date from document properties).

Office Action, Non-Final Rejection, U.S. Appl. No. 13/106,166, mail date Dec. 19, 2012.

\* cited by examiner

HIGH-CAPACITY WIDE-RANGE VARIABLE ROTATIONAL RATE VANE TESTING DEVICE

CROSS-REFERENCE TO RELATED APPLICATIONS

This application is a divisional of pending U.S. patent application Ser. No. 13/106,166 entitled HIGH-CAPACITY WIDE-RANGE VARIABLE ROTATIONAL RATE VANE TESTING DEVICE, filed on May 12, 2011, incorporated herein by reference in its entirety.

BACKGROUND

Devices and methods disclosed herein relate generally to testing devices, and more specifically, to vane shear testing devices.

Vane shear testing devices are used in geotechnical engineering for determination of undrained shear strength, including undisturbed and remolded values. They are also used to study the effects of rotational rate on strength and as a tool for measurement of viscosity and other flow properties as a function of the rotational velocity or resulting strain rate in a variety of materials and sediments. The vane sensor is one of the main sensor configurations used in commercial rheometry products, for example, but not limited to, R/S Soft Solids Tester by BROOKFIELD® Engineering. Existing vane shear testing devices can be used, for example, but not limited to, (a) as handheld devices for rapid in-situ determination of the undrained shear strength of mostly surficial sediments in situ, and (b) in a bore-hole configuration in terrestrial and marine environments, for example, in FUGRO® Seaclam and FUGRO® Halibut systems. Additionally, vane testing can be used in the laboratory on sediment specimens retrieved in coring or drill cylinders. In this application, the sediment core is split either along its length or cut into several sub-sections normal to its long axis. Vane tests can be performed on the exposed soil surface utilizing a variety of vane devices. General engineering practice typically calls for testing for the strength parameters (undrained shear strength, residual/remolded strength) at a rotation rate of 60-90 deg/min (ASTM Standard. (2005)). See "D4648 Standard Test Method for Laboratory Miniature Vane Shear Test for Saturated Fine-Grained Clayey Soil." ASTM International, West Conshohocken, Pa.

Rheometers are tools similar to vane shear devices (in certain configurations) and are used primarily in determining viscous parameters of fluids. Some rheometers, for example, R/S Soft Solids Tester by BROOKFIELD® Engineering, are adapted for testing viscous and yield properties of soft solids by utilizing a vane-shaped sensor. These instruments, however, test materials that are not normally encountered in natural environments, for example, materials that are typical to geotechnical investigations of either terrestrial or marine sediments. Thus, these instruments can be limited in rotational velocity and maximum torque capacity. These limitations could make them insufficient for certain types of geotechnical media and specific testing conditions. Further, devices characterized by variable rate torque application can be limited by the maximum rotational velocity that can be attained and the maximum torque that can be applied, limiting the use of these devices, especially for applications such as impact penetration and burial of objects in marine sediments. What is needed is an apparatus for measuring shear strength and viscosity of sediments that extends both the maximum rotational rate attainable and the maximum torque sustainable, and includes a high data acquisition rate and data storage.

SUMMARY

To address the above-stated needs, the present teachings provide an apparatus, method of making the apparatus, and method of using the apparatus for accurately measuring, for example, but not limited to, peak, evolution, and residual values of the undrained shear strength, yield, and viscous and plastic flow (including hardening and softening) characteristics of cohesive sediments at various pre-set and variable values of the rotational velocity of the vane sensor. The main purpose of the apparatus is to measure accurately undrained shear strength, yield, and viscous flow characteristics of cohesive sediments at various pre-set values of the rotational velocity of the vane or other sensor. The purpose is to extend the measurement ranges for the combination of torque and rotational velocity to beyond those achievable by any other currently existing research or commercial device available.

The apparatus is intended for direct measurements and constitutive characterization of a variety of cohesive sediments. The apparatus consists of a base on which a vertical column is mounted. The vertical column includes a linear track on which a carriage plate mounts, facilitating the mounting of the head assembly and allowing for an easy set-up and adjustment of the measurement head position. The head assembly consists of a drive motor, rotary torque sensor, and the vane sensor for insertion into the sediment sample. The carriage slides on the vertical column linear track and is supported by a counter balance assembly that uses a constant tension spring having a spring force equal to the weight of the carriage and head assembly. The counter balance assembly allows the carriage to be easily adjusted vertically thus inserting the vane into the sediment sample with required accuracy in position and minimal distortion of the sediment. The apparatus incorporates a clamping system to support a variety of standard sample tubes in which the sediment sample is contained. The motor is controlled by a computer program that includes high speed data acquisition capabilities to measure and record the torque produced by the vane as a function of time.

The apparatus is capable of testing a wide range of materials, from liquids, to semi-solids, and to solids of variable resistance to shearing, including, but not limited to, a wide variety of marine sediments. The apparatus is capable of testing at a high rotational velocity and acquiring data at a high rate. The apparatus is designed to receive sensor attachments, for example, conventional attachments manufactured by, for example, but not limited to, WYKEHAM FARRANCE™ attachments (W sensors) and BROOKFIELD® Engineering attachments (B sensors). The attachments can be coupled using, for example, adapters, and can include, for example, but not limited to, vanes, concentric cylinders, bobs, double-gap sensors, and cone and plate.

The apparatus for measuring characteristics of sediments can include, but is not limited to including a sensor drive shaft coupled to a one of a variety of sensors, for measuring characteristics, a main measurement head applying a rotation rate of up to 4000 rpm to the sensor drive shaft and determining an undrained shear strength up to 230 kPa, and a computer, coupled to the main measurement head, collecting the characteristics while the rotation rate may be greater than 1200 rpm and the undrained shear strength may be greater than 6 kPa.

DETAILED DESCRIPTION

The problems set forth above as well as further and other problems are solved by the present teachings. These solutions and other advantages are achieved by the various embodiments of the teachings described herein below.

Figure 1:
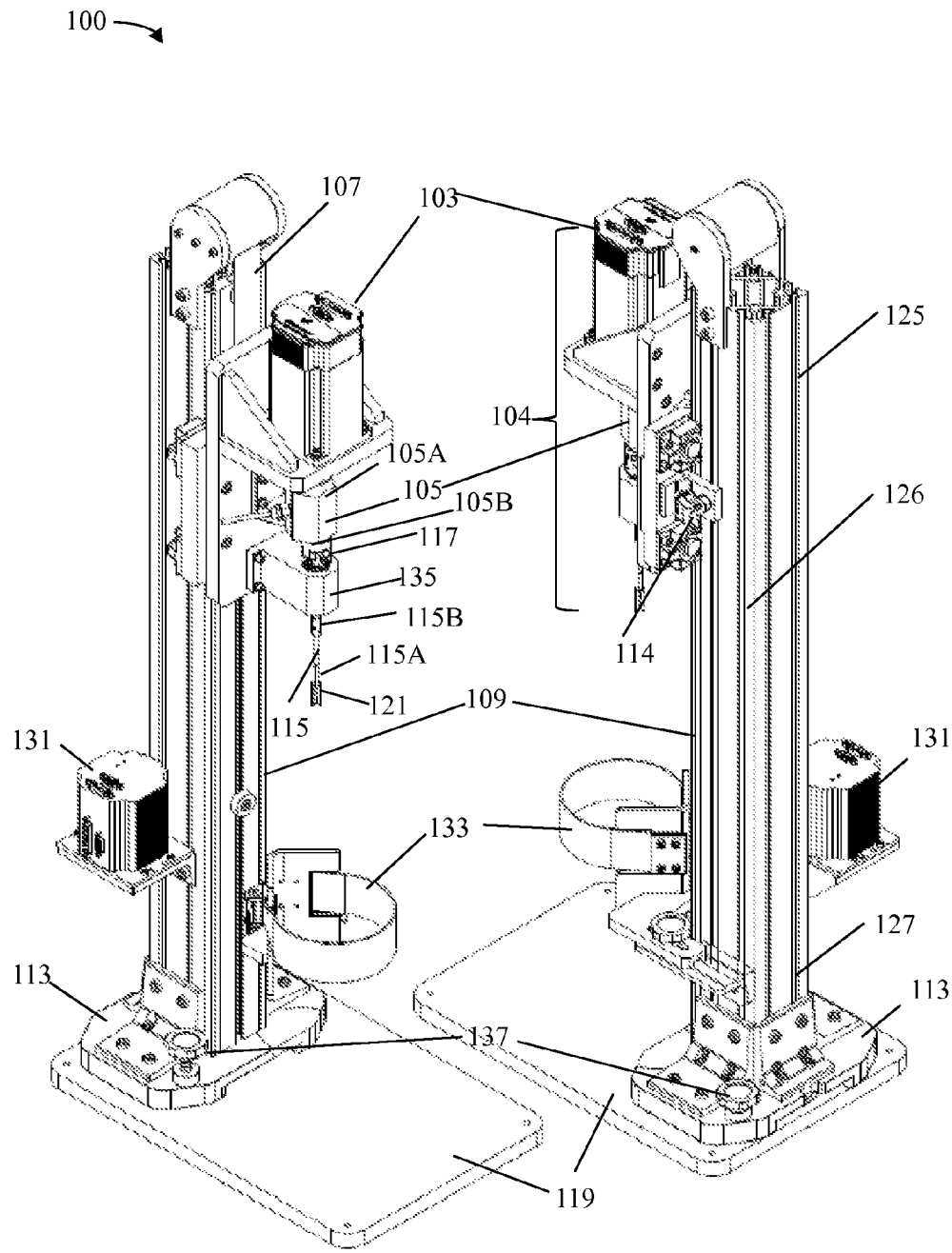
FIG. 1 is a schematic diagram front and rear isometric views of an embodiment of the apparatus of the present teachings.
Figure 2:
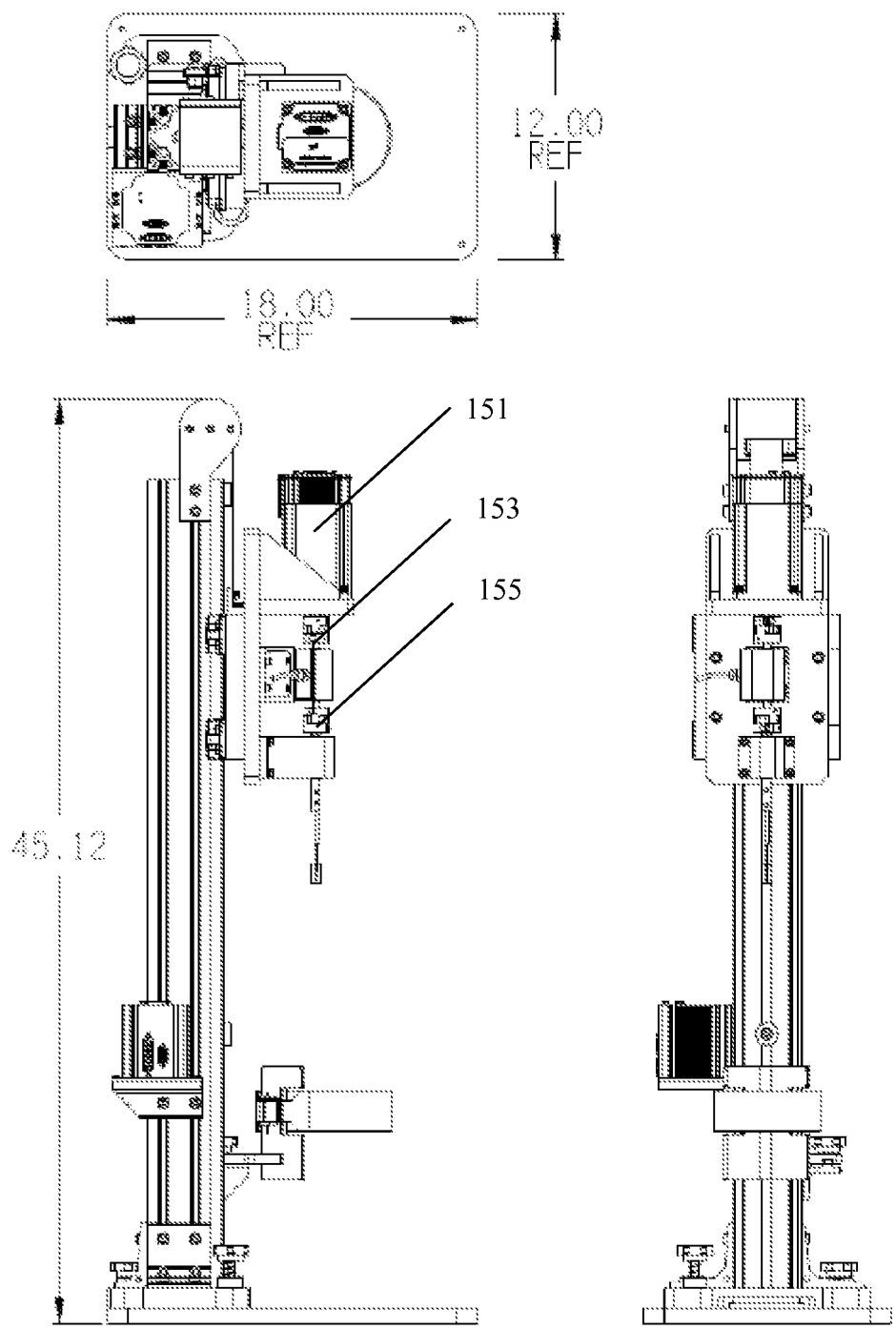
FIG. 2 is a schematic diagram of elevation and plan views of an embodiment of the apparatus of the present teachings.
Figure 3:
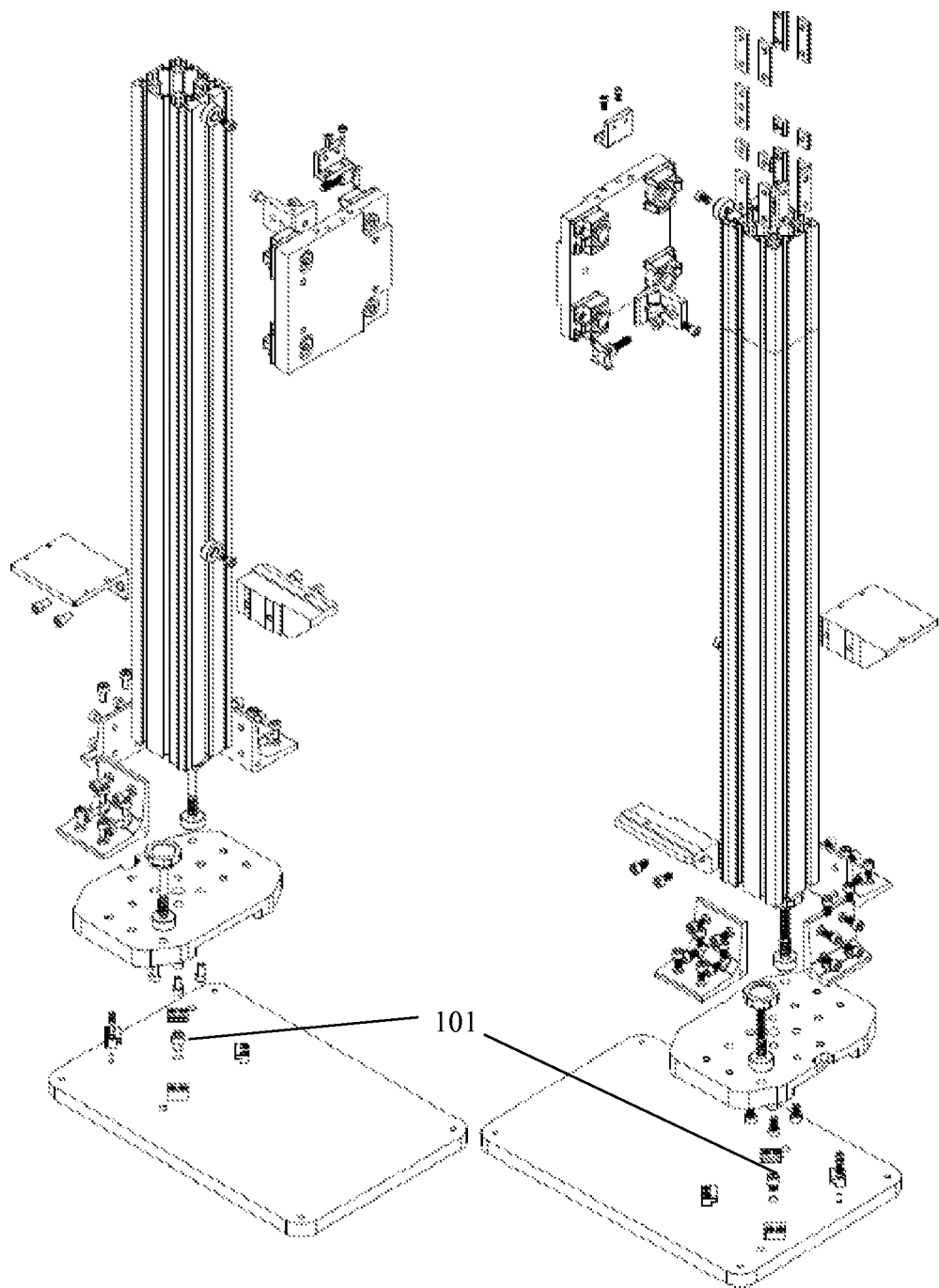
FIG. 3 is a schematic diagram of exploded front and rear views of the column assembly of an embodiment of the apparatus of the present teachings.

Referring now to FIGS. 1-3, apparatus 100 for measuring characteristics of sediments can include, but is not limited to including, main tower 109 (FIG. 1) attached to base plate 113 (FIG. 1), main measurement head 104 (FIG. 1) connected to main tower 109 (FIG. 1) by constant load spring mechanism 107 (FIG. 1), for positioning measurement head 104 (FIG. 1), said main measurement head including a drive motor 103 (FIG. 1), a motor controller 131 (FIG. 1), a load cell shaft coupled with drive motor 103 (FIG. 1) and a sensor drive shaft within a drive shaft housing 135 (FIG. 1) via a coupler 117 (FIG. 1), said load cell shaft including a load cell, a sensor 121 (FIG. 1) by attachment mechanism 115B (FIG. 1) to the sensor drive shaft, and a vessel holding a sample, said sensor 121 (FIG. 1) measuring characteristics of the sample. Sensor 121 (FIG. 1) supplies the measured characteristics to load cell 105 (FIG. 1), and load cell 105 (FIG. 1) supplies the measured characteristics to a computer. Apparatus can optionally include an attachment holder 115 (FIG. 1) coupled with attachment mechanism 115B (FIG. 1), special connector 101 (FIG. 3) rotatably coupling the base plate 113 (FIG. 1) with the main tower 109 (FIG. 1), and screws 137 (FIG. 1) fixedly coupling base plate 113 (FIG. 1) with main tower 109 (FIG. 1). Sensor 121 (FIG. 1) can be, for example, but not limited to, W sensors and B sensors. Main measurement head 104 can be configured to include torque load cell 105 (FIG. 1). Referring now primarily to FIG. 2, drive motor side view 151 (FIG. 2) shows a different perspective of drive motor 103 (FIG. 1). Torque load cell side view 153 (FIG. 2) shows a different perspective of torque load cell 105 (FIG. 1). Coupler side view 155 (FIG. 2) shows a different perspective of coupler 117 (FIG. 1)

Continuing to refer to FIGS. 1-3, apparatus 100 for conducting testing of undrained shear strength of water saturated cohesive sediments as well as viscosity of a variety of soft solids and viscous fluids can include, but is not limited to including, main tower 109 (FIG. 1) attached to base plate 113 (FIG. 1). Base plate 113 (FIG. 1) can be connected to main tower 109 (FIG. 1) by, for example, but not limited to, special connector 101 (FIG. 3) that can allow for main tower 109 (FIG. 1) to be rotated to achieve various orientations with respect to mounting base 119 (FIG. 1). Base plate 113 (FIG. 1) and main tower 109 (FIG. 1) can be, for example, fixed in position with screws 137 (FIG. 1). Main measurement head 104 (FIG. 1), which includes main motor 103 (FIG. 1) and torque load cell 105 (FIG. 1), is connected to main tower 109 (FIG. 1) by constant load spring mechanism 107 (FIG. 1), allowing for smooth and precise vertical sliding and positioning of measurement head 104 (FIG. 1) at a desired height maintained in part by counter balance 131. Load cell shaft (not shown) inside torque load cell 105 (FIG. 1), is connected to drive motor 103 (FIG. 1) on the end nearest drive motor 103 (FIG. 1) and to a sensor drive shaft (not shown) located within housing 135 (FIG. 1), and attaches at one end to the load cell shaft via coupler 117 (FIG. 1). Torque load cell 105 (FIG. 1) can be, but is not limited to being, a T8 ECO series contactless torque load cell, manufactured by Interface Co. (www.interfaceforce.com). The output of torque load cell 105 (FIG. 1) is via a DC voltage that can be acquired, recorded, and converted to engineering units via a calibration factor for torque. Torque load cell 105 (FIG. 1) can be connected to a data acquisition card, for example, via a switchboard in a computer. For example, a National Instruments DAQCard-6036E, which has a 16-bit signal resolution and can sample at 200 kHz, can be used. Coupler 117 (FIG. 1) can be, but is not limited to being, Elastomer Coupling manufactured by R+W Co. (www.rw-America.com). Couple Coupler 117 (FIG. 1) can include metal alloy housings with an elastomer inserts of various stiffnesses. These couplings can compensate for misalignment and vibration. Sensor 121 (FIG. 1) is attached, in the case of W sensors, by attachment mechanism 115B (FIG. 1). W sensors can be directly attached, whereas B sensors can be attached to attachment mechanism 115B (FIG. 1) by a separate attachment (holder) 115A (FIG. 1). Shown in FIG. 1 is a W sensor being attached by attachment mechanism 115B (FIG. 1). To attach a B sensor, a coupler that fits over attachment mechanism 115B (FIG. 1) is used, making it possible to attach a variety of B sensors. Coupler 117 (FIG. 1) appears on both sides of load cell 105 (FIG. 1). On one side, motor 103 (FIG. 1) is coupled to the load cell shaft by coupler 117 (FIG. 1) to minimize off-axis forces of load cell 105 (FIG. 1) and an increase in torque measurement accuracy. Coupler 117 (FIG. 1) can be designed with elastomer inserts selected empirically to minimize off-axis forces. The attachment of sensor 121 (FIG. 1) to the sensor drive shaft (which is located inside housing 135 (FIG. 1)) can be completed, for example, by direct attachment, using a built-in coupler for use with sensors including, but not limited to, WYKEHAM FARRANCE™ vanes, or by using an additional coupler that is attached to sensor drive shaft 115B (FIG. 1) and allows for mounting all sensors available from, for example, but not limited to, BROOKFIELD® Engineering for the Soft Solids Tester and similar rheometers. The couplers securely fasten the vanes and other sensor attachments so that the sensor (or vane) will not disengage, decouple, or slip during testing.

Referring again to FIG. 1, to operate apparatus 100, a sample is fixed at the base of the instrument via one of several available options (depending on the type and the geometry of the sample). Appropriate vane (or other sensor) is attached to the matching coupler and then to the lower portion of the load cell shaft. The main measurement head with the motor, load cell, and the mounted vane (or other sensor) are then lowered into the specimen to the desired depth and fixed in place by tightening the screws on the slider part of the vertical tower assembly. At this stage the device is ready for testing.

Testing can be conducted in a variety of ways, fully controlled via the LabView™ developed software package. This is generally (but not only) done under the conditions of the constant rotational velocity, set via the software interface at the desired value and not to exceed 4000 rpm (the motor limit). As the motor-vane assembly is turning within the specimen, load cell 105 is continuously measuring the torque.

Data acquisition software is monitoring, recording, and storing the measured torque, which is generated by the resistance of the material being tested to movement of the sensor package (vane, bob, etc.). The data acquisition software is also monitoring, recording, and storing the motor parameters, including current velocity, and position. From these measurements, a variety of parameters of interest can be derived, including undrained shear strength, residual shear strength, viscosity, yield properties, and other as a function of time, current rotational velocity, or position of the sensor within the specimen.

Referring again to FIG. 1, apparatus 100 can improve measurement capacities, including maximum torque and maximum rotational velocity that can be achieved (see Table 1) and can improve the ability to handle a variety of specimen sizes and shapes, including traditional small specimens in boxes, beakers, core sub-sections, and similar vessels, fully split long cores positioned flat on the table (base plate), or full cores or long sections of cores attached to the main tower of the device when it is rotated to the full back position. This latter position allows for testing at ends of long cores without sub-sampling or splitting and without changing the preferred vertical orientation of the core (sampling tube). Table 1 shows a comparison of device capacities of the apparatus of the present teachings compared to alternative devices.

|  | Locat & Demers '88 | Perez-Foguet et al. '99 | Biscontin & Pestana '01 | Apparatus of the present teachings |
|---|---|---|---|---|
| Max rate, rpm | 500; 1200 | 400 | 100 | 4000 |
| Max Su, kPa | 0.4, 0.05 | 0.6 | 6 | 230 |

Figure 4:
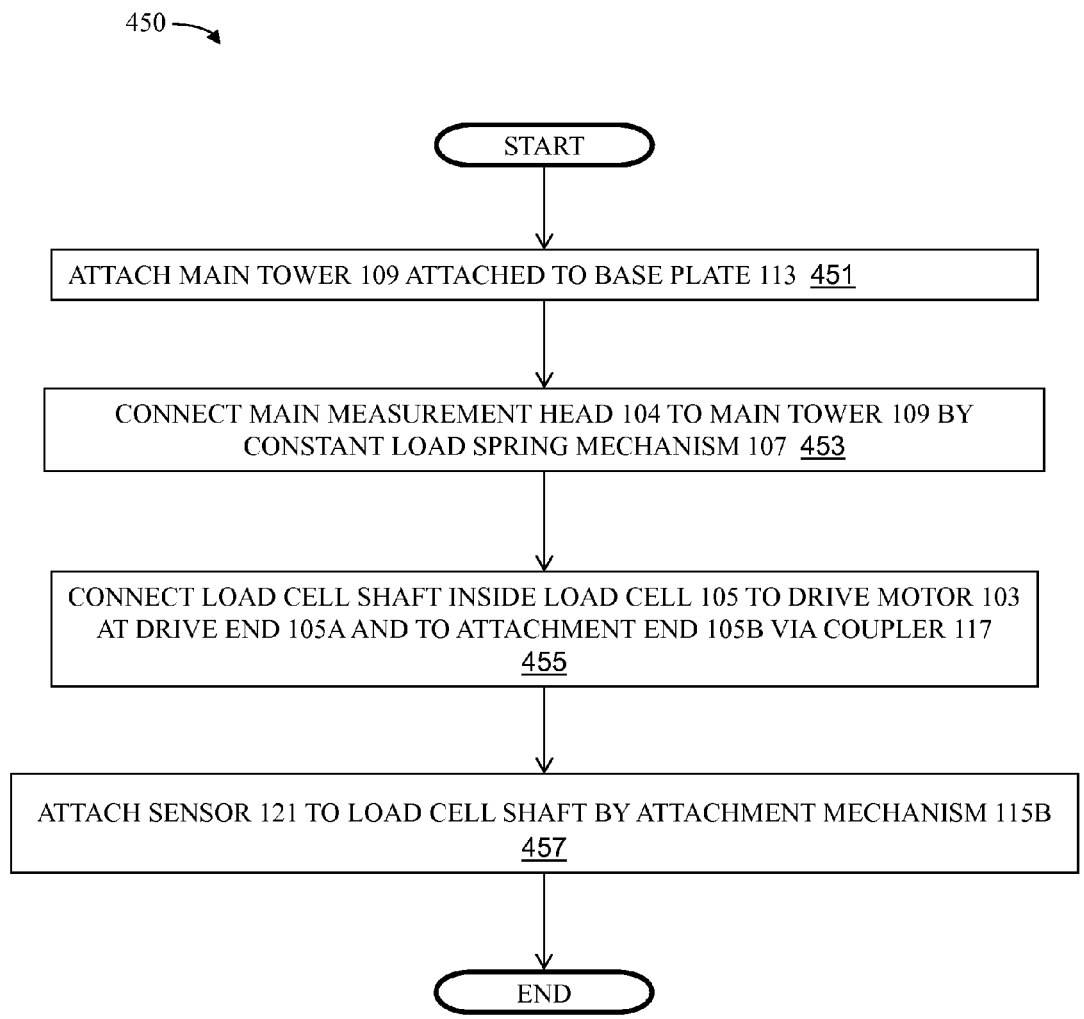
FIG. 4 is a flowchart of the method of manufacture of the apparatus of the present teachings.

Referring now primarily to FIG. 4, method 450 (FIG. 4) for manufacturing an apparatus for measuring characteristics of sediments can include, but is not limited to including, the steps of attaching 451 (FIG. 4) main tower 109 (FIG. 1) to base plate 113 (FIG. 1), connecting 453 (FIG. 4) main measurement head 104 (FIG. 1) to main tower 109 (FIG. 1) by constant load spring mechanism 107 (FIG. 1), connecting 455 (FIG. 4) load cell shaft inside load cell 105 (FIG. 1) in main measurement head 104 (FIG. 1) to drive motor 103 (FIG. 1) at drive end 105A (FIG. 1) and to attachment end 105B (FIG. 1) via coupler 117 (FIG. 1), and attaching 457 (FIG. 4) sensor 121 (FIG. 1) to load cell shaft by attachment mechanism 115B (FIG. 1). Optional steps can include attaching W sensors directly to attachment mechanism 115B (FIG. 1), attaching B sensors to attachment mechanism 115B (FIG. 1) using a coupler covering attachment mechanism 115B (FIG. 1), selecting the sensors from a group consisting of WYKEHAM FARRANCE™ vanes and BROOKFIELD® Engineering rheometers, connecting base plate 113 (FIG. 1) rotatably to main tower 109 (FIG. 1), fixing base plate 113 (FIG. 1) and main tower 109 (FIG. 1) in position with screws 137 (FIG. 1), and configuring main measurement head 104 (FIG. 1) with main motor 103 (FIG. 1) and torque load cell 105 (FIG. 1).

Figure 5:
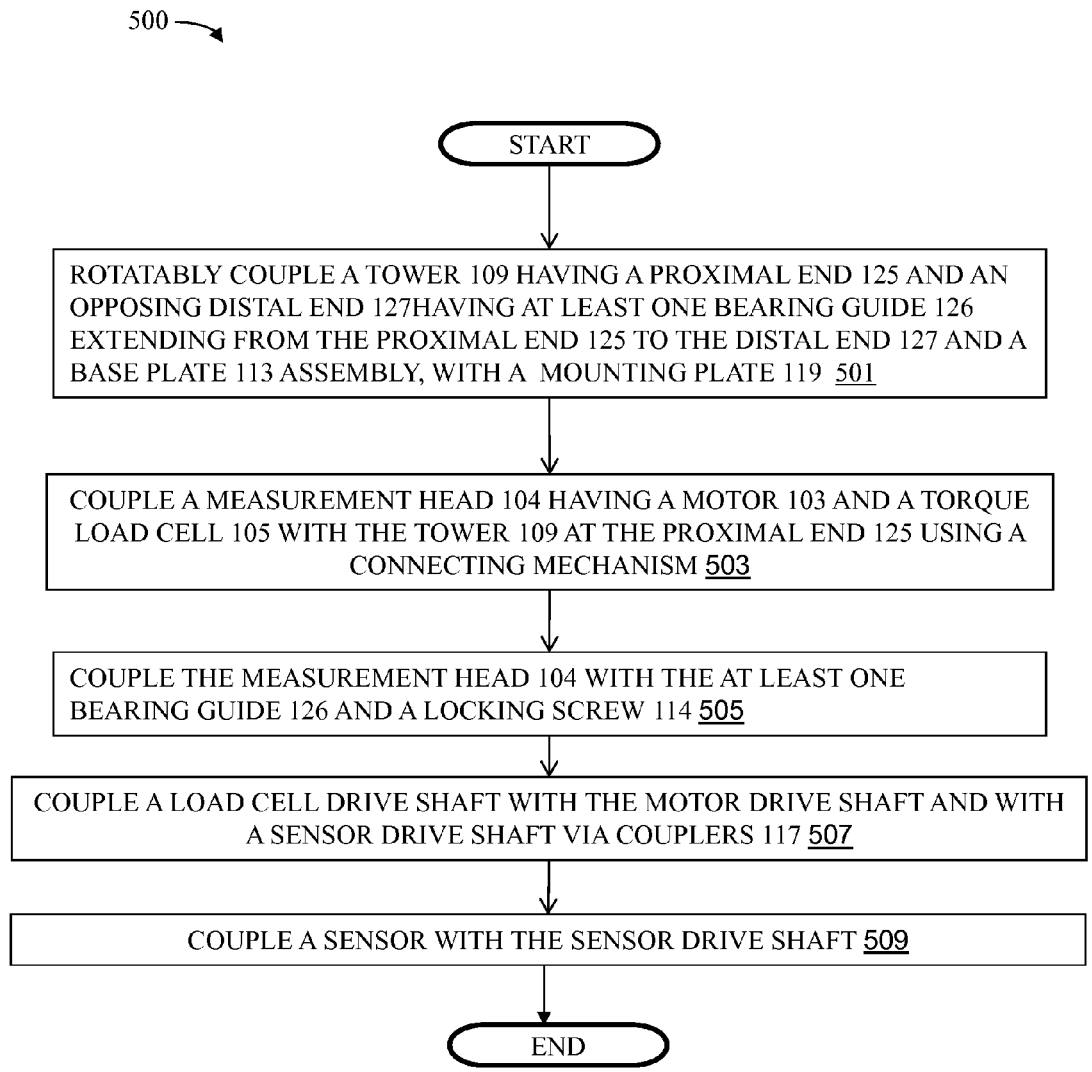
FIG. 5 is a flowchart of an alternate method of manufacture of the apparatus of the present teachings.

Referring now primarily to FIG. 5, alternative method 500 (FIG. 5) for manufacturing an apparatus for measuring characteristics of sediments can include, but is not limited to including, the steps of rotatably 501 (FIG. 5) coupling tower 109 (FIG. 1) having proximal end 125 (FIG. 1) and opposing distal end 127 (FIG. 1), having at least one bearing guide 126 (FIG. 1) extending from proximal end 125 (FIG. 1) to distal end 127 (FIG. 1) and base plate 113 (FIG. 1) assembly, with mounting plate 119 (FIG. 1), coupling 503 (FIG. 5) measurement head 104 (FIG. 1) having motor 103 (FIG. 1) and torque load cell 105 (FIG. 1) with tower 109 (FIG. 1) at proximal end 125 (FIG. 1) using a connecting mechanism, motor 103 (FIG. 1) having a motor drive shaft, coupling 505 (FIG. 5) measurement head 104 (FIG. 1) with at least one bearing guide 126 (FIG. 1) and locking screw 114 (FIG. 1), coupling 507 (FIG. 5) a load cell drive shaft with the motor drive shaft and with a sensor drive shaft via couplers 117 (FIG. 1), and coupling 509 (FIG. 5) a sensor with the sensor drive shaft. Optional steps can include fixing base plate 113 (FIG. 1) in place with screws 137 (FIG. 1), mounting height-adjustable specimen holder 133 (FIG. 1) on tower 109 (FIG. 1), and mounting girth-adjustable specimen holder 133 (FIG. 1) on tower 109 (FIG. 1). The connecting mechanism can be a spring mechanism, and the spring mechanism can be constant load. The couplers can be flexible.

Figure 6:
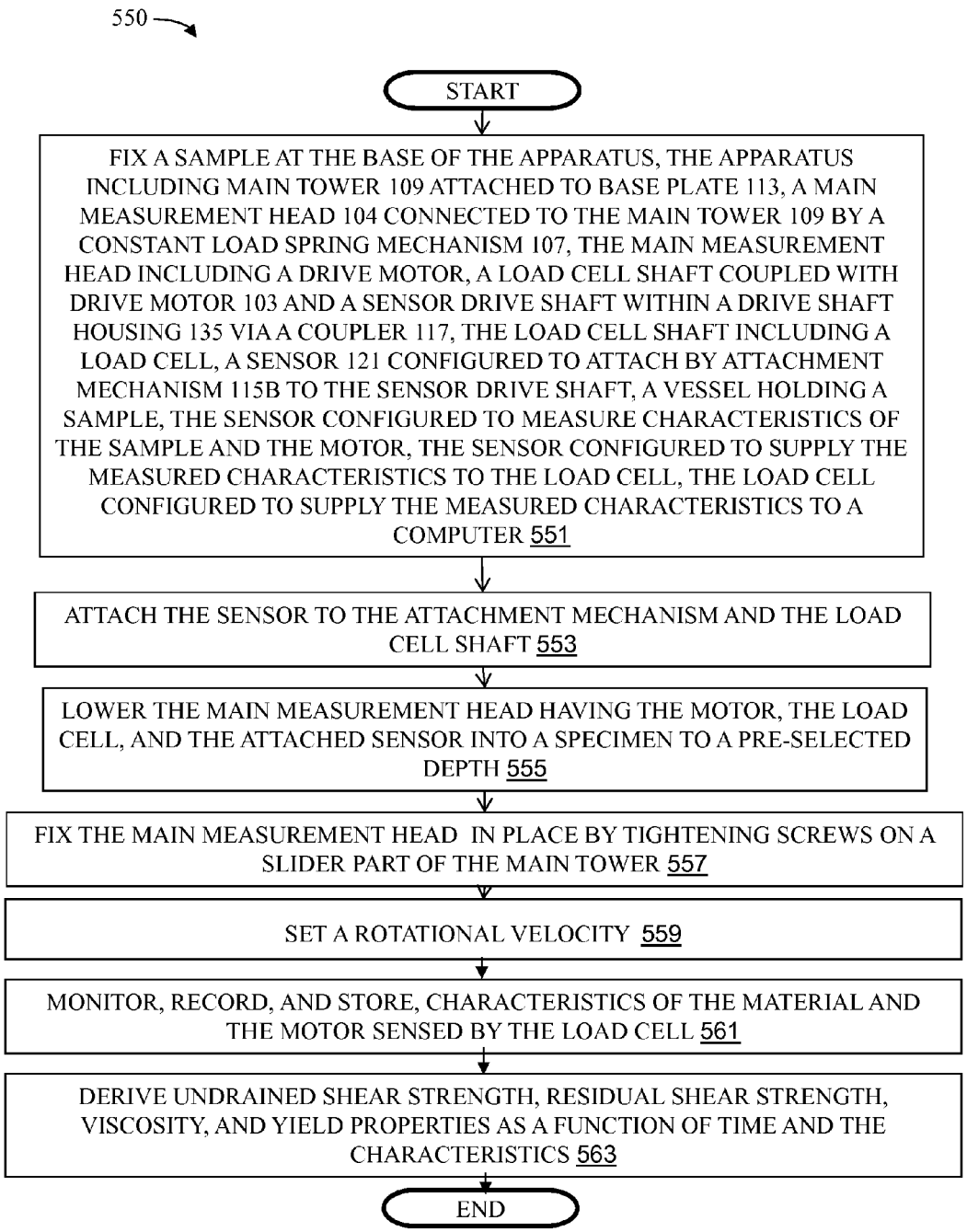
FIG. 6 is a flowchart of the method of use of the apparatus of the present teachings.

Referring now primarily to FIG. 6, method 550 (FIG. 6) for using an apparatus for measuring characteristics of materials can include, but is not limited to including the steps of fixing 551 (FIG. 6) a sample at the base of the apparatus, the apparatus including main tower 109 (FIG. 1) attached to base plate 113 (FIG. 1), a main measurement head 104 (FIG. 1) connected to the main tower 109 (FIG. 1) by a constant load spring mechanism 107 (FIG. 1), the main measurement head including a drive motor, a load cell shaft coupled with drive motor 103 and a sensor drive shaft within a drive shaft housing 135 (FIG. 1) via a coupler 117 (FIG. 1), the load cell shaft including a load cell, a sensor 121 (FIG. 1) configured to attach by attachment mechanism 115B (FIG. 1) to the sensor drive shaft, a vessel holding a sample, the sensor configured to measure characteristics of the sample and the motor, the sensor configured to supply the measured characteristics to the load cell, the load cell configured to supply the measured characteristics to a computer, attaching 553 (FIG. 6) the sensor to the attachment mechanism and the load cell shaft, lowering 555 (FIG. 6) the main measurement head having the motor, the load cell, and the attached sensor into a specimen to a pre-selected depth, fixing 557 (FIG. 6) the main measurement head in place by tightening screws on a slider part of the main tower, setting 559 (FIG. 6) a rotational velocity, monitoring, recording, and storing 561 (FIG. 6) characteristics of the material and the motor sensed by the load cell, and deriving 563 (FIG. 6) undrained shear strength, residual shear strength, viscosity, and yield properties as a function of time and the characteristics. The characteristics can include, but are not limited to including, torque generated by the resistance of the material to movement of the sensor, motor current velocity, motor position, and motor torque.

Referring again to FIG. 1, apparatus 100 has, in comparison to existing technology, high torque capacity, high velocity, digitally controlled and monitored motor, high precision, infinite-rotation load-cell for accurate torque measurements at variety of speeds, load-compensated sliding head lift mechanism for easier and more precise placement of the sensor (vane) in the testing medium, rotating design for the main assembly tower, allowing for testing of small core sub-section and other specimens in small containers, full spit cores, and long upright positioned cores without sub-sectioning (main tower in rotated back position), high speed data acquisition and control system and software written using, for example, but not limited to, a LABVIEW® package, and the ability to accept different sensors, for example, but not limited to, via two specially designed couples, including standard WYKEHAM FARRANCE™ vanes, and sensors supplied by BROOKFIELD® Engineering R/S Soft Solids Tester (vane, concentric cylinder, cup and plate, etc.). Apparatus 100 can include, but is not limited to including, National Instruments DAQCard-6036E (having 16-bit resolution, 200 kHz acquisition rate) and National Instruments LabView software. The commercial software is augmented by acquisition software in which data are acquired at a maximum rate of, for example, 200 kHz, and conditioned and time-averaged to manage natural fluctuations and noise. The acquisition software can increase data accuracy by filtering out or smoothing out the electrical noise. For example, using a moving average of 20 would yield approximately 0.42 data points per degree rotation at a maximum angular velocity of 4000 rpm. This corresponds to approximately a 2.4° rotation per measurement. In this example, the frequency of measurements is sufficient for accurate results in geologic materials. Apparatus 100 can also store the acquired and filtered/conditioned data on conventional mass storage devices (not shown).

The present embodiment is directed, in part, to software for accomplishing the methods discussed herein, and computer readable media storing software for accomplishing these methods. The various modules described herein can be accomplished on the same CPU, or can be accomplished on different computers. In compliance with the statute, the present embodiment has been described in language more or less specific as to structural and methodical features. It is to be understood, however, that the present embodiment is not limited to the specific features shown and described, since the means herein disclosed comprise preferred forms of putting the present embodiment into effect.

Referring again primarily to FIG. 6, method 550 can be, in whole or in part, implemented electronically. Signals representing actions taken by elements of apparatus 100 (FIG. 1) and other disclosed embodiments can travel over at least one live communications network. Control and data information can be electronically executed and stored on at least one computer-readable medium. Components of the apparatus can be implemented to execute on at least one computer node in at least one live communications network. Common forms of a computer-readable medium can include, for example, but not be limited to, a floppy disk, a flexible disk, a hard disk, magnetic tape, or any other magnetic medium, a compact disk read only memory or any other optical medium, punched cards, paper tape, or any other physical medium with patterns of holes, a random access memory, a programmable read only memory, and erasable programmable read only memory (EPROM), a Flash EPROM, or any other memory chip or cartridge, or any other medium from which a computer can read. Further, the computer readable medium can contain graphs in any form including, but not limited to, Graphic Interchange Format (GIF), Joint Photographic Experts Group (JPEG), Portable Network Graphics (PNG), Scalable Vector Graphics (SVG), and Tagged Image File Format (TIFF).

Although the present teachings have been described with respect to various embodiments, it should be realized these teachings are also capable of a wide variety of further and other embodiments.

What is claimed as new and desired to be protected by Letters Patent of the United States is:

1. A method for manufacturing an apparatus for measuring characteristics of sediments comprising:
   rotatably coupling a tower with a mounting plate, the tower having a proximal end and an opposing distal end, the tower having at least one bearing guide and a base plate assembly;
   coupling a measurement head having a motor and a torque load cell with the tower at the proximal end using a connecting mechanism, the motor having a motor drive shaft;
   coupling the measurement head with the at least one bearing guide and a locking screw;
   coupling a load cell drive shaft with the motor drive shaft and with a sensor drive shaft via couplers; and
   coupling a sensor with the sensor drive shaft.

2. The method as in claim 1 further comprising:
   fixing the base plate in place.

3. The method as in claim 1 wherein the connecting mechanism is a spring mechanism.

4. The method as in claim 3 further comprising:
   positioning the main measurement head using the spring mechanism.

5. The method as in claim 3 wherein the spring mechanism is constant load.

6. The method as in claim 1 wherein the couplers are flexible couplers.

7. The method as in claim 1 further comprising:
   mounting a height-adjustable specimen holder on the tower.

8. The method as in claim 1 further comprising:
   mounting a girth-adjustable specimen holder on the tower.

9. The method as in claim 1 further comprising:
   attaching W sensors to an attachment mechanism coupled with the sensor drive shaft.

10. The method as in claim 9 further comprising:
    attaching B sensors to the attachment mechanism using a cover over the attachment mechanism.

11. The method as in claim 1 further comprising:
    selecting the sensor from a group consisting of WYKEHAM FARRANCE™ vanes and BROOKFIELD® Engineering rheometers.

12. The method as in claim 1 further comprising:
    fixing the base plate assembly and the main tower in position with screws.

13. The method as in claim 1 further comprising:
    coupling the sensor to a computer capable of receiving data from the sensor.

14. The method as in claim 1 further comprising:
    testing the apparatus by applying to the load cell drive shaft, by the measurement head, a rotation rate of up to about 4000 rpm to determine an undrained shear strength.

15. A system for manufacturing an apparatus for measuring characteristics of sediments comprising:
    means for rotatably coupling a tower with a mounting plate, the tower having a proximal end and an opposing distal end, the tower having at least one bearing guide and a base plate assembly;
    means for coupling a measurement head having a motor and a torque load cell with the tower at the proximal end using a connecting mechanism, the motor having a motor drive shaft;
    means for coupling the measurement head with the at least one bearing guide and a locking screw;
    means for coupling a load cell drive shaft with the motor drive shaft and with a sensor drive shaft via couplers; and
    means for coupling a sensor with the sensor drive shaft.

16. The method as in claim 1 wherein the connecting mechanism is a spring mechanism.

17. The method as in claim 1 further comprising:
    means for mounting a height-adjustable specimen holder on the tower.

18. The method as in claim 1 further comprising:
    means for mounting a girth-adjustable specimen holder on the tower.

19. The method as in claim 1 further comprising the step of:
means for attaching the sensors to an attachment mechanism coupled with the sensor drive shaft.

20. The method as in claim 1 further comprising:
means for coupling the sensor to a computer capable of receiving data from the sensor.

* * * * *